(12) United States Patent
Kandori et al.

(10) Patent No.: US 11,064,914 B2
(45) Date of Patent: Jul. 20, 2021

(54) BRAIN DYSFUNCTION EVALUATION SYSTEM, BRAIN DYSFUNCTION EVALUATION METHOD, AND PROGRAM

(71) Applicant: MAXELL, LTD., Kyoto (JP)

(72) Inventors: Akihiko Kandori, Tokyo (JP); Yuko Sano, Tokyo (JP)

(73) Assignee: MAXELL, LTD., Tokyo (JP)

( * ) Notice: Subject to any disclaimer, the term of this patent is extended or adjusted under 35 U.S.C. 154(b) by 323 days.

(21) Appl. No.: 15/507,020

(22) PCT Filed: Jun. 12, 2015

(86) PCT No.: PCT/JP2015/066997
§ 371 (c)(1),
(2) Date: Feb. 27, 2017

(87) PCT Pub. No.: WO2016/031348
PCT Pub. Date: Mar. 3, 2016

(65) Prior Publication Data
US 2017/0251956 A1    Sep. 7, 2017

(30) Foreign Application Priority Data
Aug. 29, 2014  (JP) .............................. JP2014-176434

(51) Int. Cl.
*A61B 5/11*    (2006.01)
*A61B 5/00*    (2006.01)

(52) U.S. Cl.
CPC .......... *A61B 5/1124* (2013.01); *A61B 5/0022* (2013.01); *A61B 5/11* (2013.01);
(Continued)

(58) Field of Classification Search
CPC ....... A61B 5/1124; A61B 5/11; A61B 5/4088; A61B 5/6826; A61B 5/4064;
(Continued)

(56) References Cited

U.S. PATENT DOCUMENTS

| 5,885,231 A * | 3/1999 | Cramer ................ A61B 5/1124 |
| | | 600/587 |
| 2002/0192624 A1* | 12/2002 | Darby ...................... A61B 5/16 |
| | | 434/236 |

(Continued)

FOREIGN PATENT DOCUMENTS

| JP | 2007-301003 A | 11/2007 |
| JP | 2008-246126 A | 10/2008 |

(Continued)

OTHER PUBLICATIONS

International Search Report for WO 2016/031348 A1, dated Sep. 1, 2015.
(Continued)

*Primary Examiner* — Devin B Henson
(74) *Attorney, Agent, or Firm* — Volpe Koenig

(57) ABSTRACT

A system for evaluating the degree of brain dysfunction of a subject, such as a decline in cognitive function, calculates a difference in movement functions between both hands in a coordination movement. The system includes a storage device for storing time-series data on a finger movement task of each of both hands of a test subject acquired by a movement sensor; a data processing device for analyzing the time-series data stored in the storage device; and a display device for displaying an analysis result analyzed by the data processing device. The data processing device includes a movement waveform generation unit for generating a movement waveform corresponding to the time-series data stored in the storage device; and a difference-between-hands feature quantity generation unit for generating a difference-between-hands feature quantity which represents a difference in respective finger movement tasks between both hands, based on the respective movement waveforms of both hands.

2 Claims, 16 Drawing Sheets

(52) U.S. Cl.
CPC .......... *A61B 5/4088* (2013.01); *A61B 5/6826* (2013.01); *A61B 5/7257* (2013.01); *A61B 2562/0257* (2013.01)

(58) Field of Classification Search
CPC ... A61B 5/1125; A61B 5/0022; A61B 5/7257; A61B 5/7235
See application file for complete search history.

(56) References Cited

U.S. PATENT DOCUMENTS

| | | | |
|---|---|---|---|
| 2007/0272599 A1* | 11/2007 | Miyashita | A61B 5/1101 209/527 |
| 2008/0238414 A1 | 10/2008 | Miyashita et al. | |
| 2009/0118648 A1* | 5/2009 | Kandori | A61B 5/1107 600/595 |
| 2009/0192418 A1 | 7/2009 | Miyashita et al. | |

FOREIGN PATENT DOCUMENTS

| | | |
|---|---|---|
| JP | 2011-083403 A | 4/2011 |
| JP | 2012-217797 A | 11/2012 |
| JP | 2013-255786 A | 12/2013 |

OTHER PUBLICATIONS

Robbins T. W. et al., "Cambridge Neuropsychological Test Automated Battery (CANTAB): a factor analytic study of a large sample of normal elderly volunteers", Dementia and Geriatric Cognitive Disorders, Switzerland, 1994 vol. 5, No. 5, pp. 266-281, Abstract Only.

* cited by examiner

FIG.5A

| Feature Quantity No. | Name | Definition |
|---|---|---|
| 5001 | maximum amplitude of distance waveform | maximum value of local maximal values of distance waveform in entire measurement time |
| 5002 | total travel distance of distance waveform | value obtained by integrating absolute values of differential values of distance waveform through entire measurement time |
| 5003 | maximum value of calibration of distance waveform | distance value calculated from voltage when thumb and index finger are extended to maximum at calibration |
| 5004 | average of local maximal values of distance waveform | average value of local maximal values of distance waveform in entire measurement time |
| 5005 | standard deviation of local maximal values of distance waveform | standard deviation of local maximal values of distance waveform in entire measurement time |
| 5006 | slope of approximate straight line of local maximal points of distance waveform | slope of approximate straight line of local maximal points of distance waveform |
| 5007 | maximum amplitude of velocity waveform | maximum value of local maximal values of velocity waveform in entire measurement time |
| 5008 | average of maximum values of velocity waveform in opening motion | average value of maximum values of velocities in opening motion through entire measurement time |
| 5009 | average of minimum values of velocity waveform in closing motion | average value of minimum values of velocities in closing motion through entire measurement time |
| 5010 | standard deviation of maximum values of velocity waveform in opening motion | standard deviation of maximum values of velocities in opening motion through entire measurement time |
| 5011 | standard deviation of minimum values of velocity waveform in closing motion | standard deviation of minimum values of velocities in closing motion through entire measurement time |
| 5012 | energy balance of velocity waveform | ratio of: square sum of velocity when velocity takes positive value; to square sum of velocity when velocity takes negative value, in entire measurement time |
| 5013 | total energy value of velocity waveform | square sum of velocity in entire measurement time |
| 5014 | maximum amplitude of acceleration waveform | maximum value of local maximal values of acceleration waveform in entire measurement time |

FIG.5B

| 5015 | average of maximum values of acceleration waveform in opening motion | average value of maximum values of accelerations in opening motion through entire measurement time |
|---|---|---|
| 5016 | average of minimum values of acceleration waveform in opening motion | average value of minimum values of accelerations in opening motion through entire measurement time |
| 5017 | average of maximum values of acceleration waveform in closing motion | standard deviation of maximum values of accelerations in closing motion through entire measurement time |
| 5018 | average of minimum values of acceleration waveform in closing motion | standard deviation of minimum values of accelerations in closing motion through entire measurement time |
| 5019 | tapping count | number of local minimal points of distance waveform during measurement time |
| 5020 | average value of tap intervals | value obtained by dividing measurement time by tapping count 5019 |
| 5021 | average frequency of tap intervals | inverse number of average value 5020 of tap intervals |
| 5022 | standard deviation of tap intervals | standard deviation of lengths of periods of finger-to-thumb tapping during entire measurement time |
| 5023 | zero crossing count of velocity waveform | value obtained by subtracting count when velocity changes from positive value to negative value, from tapping count, during entire measurement time |
| 5024 | zero crossing count of acceleration waveform | value obtained by subtracting tapping count, from number of times that acceleration changes from positive value to negative value, from during entire measurement time |
| 5025 | local standard deviation of local maximal values of distance waveform | average value of standard deviations of "n" neighboring local maximal values of distance waveform through entire measurement time |
| 5026 | local standard deviation of tap intervals | average value of standard deviations of "n" neighboring tap intervals through entire measurement time |
| 5027 | skewness of distribution of tap intervals | skewness of frequency distribution of tap intervals in entire measurement time |
| 5028 | peakedness near local maximal point | average value of peakednesses of local maximal points of distance waveform through entire measurement time |
| 5029 | stability of time delay trajectory | stability of trajectory (attractor) of $X(t)$ and $X(t+k)$ |

FIG.7A
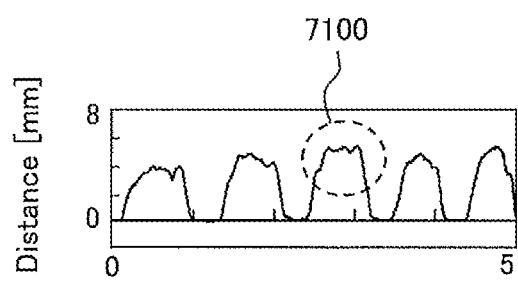
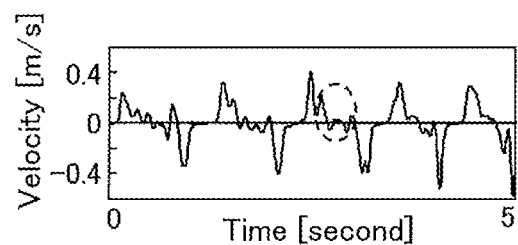
FIG.7B
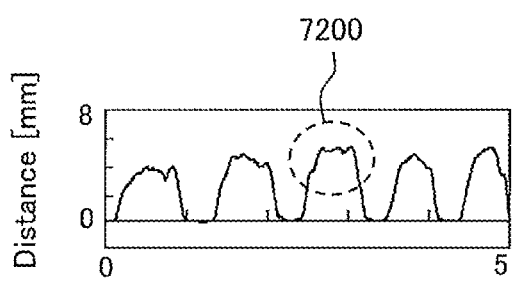
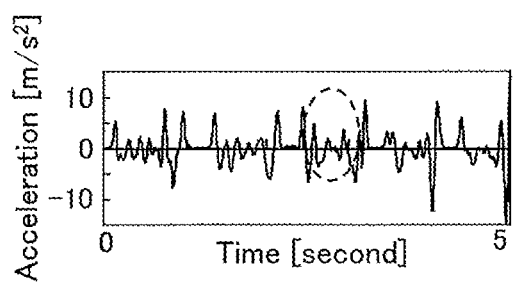

Healthy elderly subject

Nondominant hand        Dominant hand

Dementia patient

Nondominant hand        Dominant hand

FIG.13

| Entry Screen of Test Subject Information | |
|---|---|
| Please enter test subject information. | |

Test subject ID [_____] — 13100
Name [_____] — 13200
Birth date [__] [__] [_____] — 13300
Sex ⊙ male ○ female
Handedness ⊙ right ○ left ○ both ○ unknown — 13400
Remarks [_____] — 13500

[Save] — 13600

BRAIN DYSFUNCTION EVALUATION SYSTEM, BRAIN DYSFUNCTION EVALUATION METHOD, AND PROGRAM

CROSS REFERENCE TO RELATED APPLICATION

This application is a National Stage Application of PCT/JP2015/066997, filed on Jun. 12, 2015, and which application is incorporated herein by reference. To the extent appropriate, a claim of priority is made to the above disclosed application.

TECHNICAL FIELD

The present invention relates to a technique of evaluating a degree of brain dysfunction such as a decline in cognitive function.

BACKGROUND ART

With a progress of aging society, the number of cases of dementia is increasing these years. The number of dementia patients in Japan is currently estimated at as many as about two millions. Dementia may cause memory difficulty, disorientation, learning disorder, and the like, which interfere with everyday activities. In some cases, symptoms include behavioral problems such as verbal abuse, aggressive behavior, wandering, and filthy behavior. In a late stage of dementia, the patient may have movement disorder such as walking in short steps and having a droopy posture, and eventually becomes bedridden.

There are three main types of dementia: Alzheimer's disease, cerebrovascular dementia and Lewy body dementia. In other types of dementia, cognitive impairment sometimes occurs with movement disorder associated with Parkinson's disease or the like and mental disorder associated with depression, schizophrenia, or the like. Only after a definitive diagnosis of which type of dementia a patient has is made, appropriate therapy adapted to the diagnosed type can be provided such as medication treatment. Development of any types of dementia can be controlled keeping it at a stage of mild cognitive impairment, if the disease is diagnosed at an early stage and appropriate medication is administered. There is thus a need for a screening test of detecting dementia early, targeting healthy elderly people who are more likely to develop dementia.

Major dementia diagnostic measures are tests of cognitive functions including memory and judgment, such as Hasegawa's dementia scale and MMSE (Mini Mental State Examination). Those diagnostic measures require, however, that a medical doctor conducts a face-to-face test for several to several tens of minutes. From a viewpoint of restriction in time, those measures may not be suited for a screening test for a large number of test subjects.

Another diagnostic measure is a diagnosis by means of brain image measurement, which includes: a technique of examining whether or not there is brain shrinkage using CT (Computed Tomography) or MRI (Magnetic Resonance Imaging); and a technique of detecting how much amyloid beta which is considered to cause dementia is accumulated, using SPECT (Single Photon Emission Computed Tomography) or PET (Positron Emission Tomography). The brain image measurement described above requires, however, a high test fee and a long test time. The above-described measure may not be thus suited for a screening test for a large number of test subjects.

Besides the cognitive function test and the brain image measurement described above, findings are that measurement of hand finger movement can detect a decline in cognitive function. It is thought in general that cognitive impairment makes it difficult to perform cooperative movement of four limbs or body movement in response to external stimulus. Such a decreased function in body movement is likely to be observed especially in a hand finger which conducts a movement with high dexterity, even in an early stage. Dementia is thus likely to be detected in an early stage, based on a result of measurement of the finger movement using electronic equipment or the like.

Some related arts such as, for example, Patent Document 1, Patent Document 2, Patent Document 3, and Non-Patent Document 1 disclose an evaluation system for assessing cognitive function of a test subject in a simplified manner without depending on a medical doctor. The evaluation system uses a device capable of easily measuring finger movement, such as a button press device, a tablet computer, and a magnetic sensor. Patent Document 4 proposes a technique of representing a decline in cognitive function, by evaluating a phase difference in finger-to-thumb tapping (repeated opening and closing movement of two fingers (a thumb and an index finger, for example)) of each of both hands.

RELATED ART DOCUMENT

Patent Documents

Patent Document 1: Japanese Laid-Open Patent Application, Publication No. 2012-217797
Patent Document 2: Japanese Laid-Open Patent Application, Publication No. 2011-083403
Patent Document 3: Japanese Laid-Open Patent Application, Publication No. 2008-246126
Patent Document 4: Japanese Laid-Open Patent Application, Publication No. 2007-301003

Non-Patent Document

Non-Patent Document 1: Robbins T. W. et al., "Cambridge Neuropsychological Test Automated Battery (CANTAB): a factor analytic study of a large sample of normal elderly volunteers", Dementia and Geriatric Cognitive Disorders, Switzerland, 1994, Vol. 5, No. 5, pp. 266-281

SUMMARY OF THE INVENTION

Problems to be Solved by the Invention

As a decline in cognitive function progresses, a difference in movement functions between both hands is considered to become larger. Thus, a method of calculating a difference in movement functions between both hands is effective in evaluating cognitive impairment. In this regard, the techniques disclosed in Patent Document 1, Patent Document 2, Patent Document 3, and Non-Patent Document 1 describe measurement of a finger movement task with one hand. As will be understood, those Documents fail to evaluate a difference in movement functions between both hands. Patent Document 4 proposes the technique of evaluating a phase difference in finger-to-thumb tapping between both hands. Patent Document 4, however, fails to explicitly calculate a difference in movement functions between both hands which cannot achieve the above-described method.

In light of the described above, the present invention has been made in an attempt to easily evaluate a degree of brain dysfunction such as a decline in brain dysfunction by calculating a difference in movement functions between both hands when a subject performs a both hands coordination movement.

Means for Solving the Problem

In order to solve the problems the present invention has been made in an attempt to provide: a brain dysfunction evaluation system, including: a storage unit configured to store therein time-series data on a finger movement task of each of both hands of a test subject, the time-series data being acquired by a movement sensor; an analysis unit configured to analyze the time-series data stored in the storage unit; and a display unit configured to display an analysis result analyzed by the analysis unit. The analysis unit includes: a movement waveform generation unit configured to generate a movement waveform corresponding to the time-series data stored in the storage unit; and a difference-between-hands feature quantity generation unit configured to generate a difference-between-hands feature quantity which represents a difference in respective finger movement tasks between both hands of the test subject, based on the generated respective movement waveforms of both hands.

Other means for solving the problems will be described hereinafter.

Effects of the Present Invention

The present invention makes it possible to easily evaluate a degree of brain dysfunction such as a decline in cognitive function, by calculating a difference in movement functions between both hands in a both hands coordination movement.

BRIEF DESCRIPTION OF THE DRAWINGS

FIGS. 5A and 5B are a table illustrating a plurality of feature quantities acquired from the movement waveform.

FIG. 7A is an explanatory diagram illustrating a zero crossing count of a velocity waveform. FIG. 7B is an explanatory diagram illustrating a zero crossing count of an acceleration waveform.

FIG. 10A is each a diagram illustrating a trajectory of a healthy elderly subject. FIG. 10B is each a diagram illustrating a trajectory of a dementia patient.

FIG. 11A is the diagram when both hands synchronized finger tapping was performed. FIG. 11B is the diagram when both hands alternating finger tapping was performed.

FIG. 13 is a diagram illustrating a test subject information entry screen.

EMBODIMENTS FOR CARRYING OUT THE INVENTION

An embodiment for carrying out the present invention (which is hereinafter referred to as an embodiment) is described in detail below with reference to related drawings.

In this embodiment to be described below, the terms "brain dysfunction" collectively refer to all those may cause a decline in so-called cognitive function (for example, Alzheimer's disease, cerebrovascular dementia, Lewy body dementia, Parkinson's disease, hydrocephalus, depression, and schizophrenia), which also includes movement disorder caused by cerebral apoplexy or the like. To simplify explanation in the embodiment, the brain dysfunction may also be referred to as dementia.

[Entire Configuration]

Figure 1:
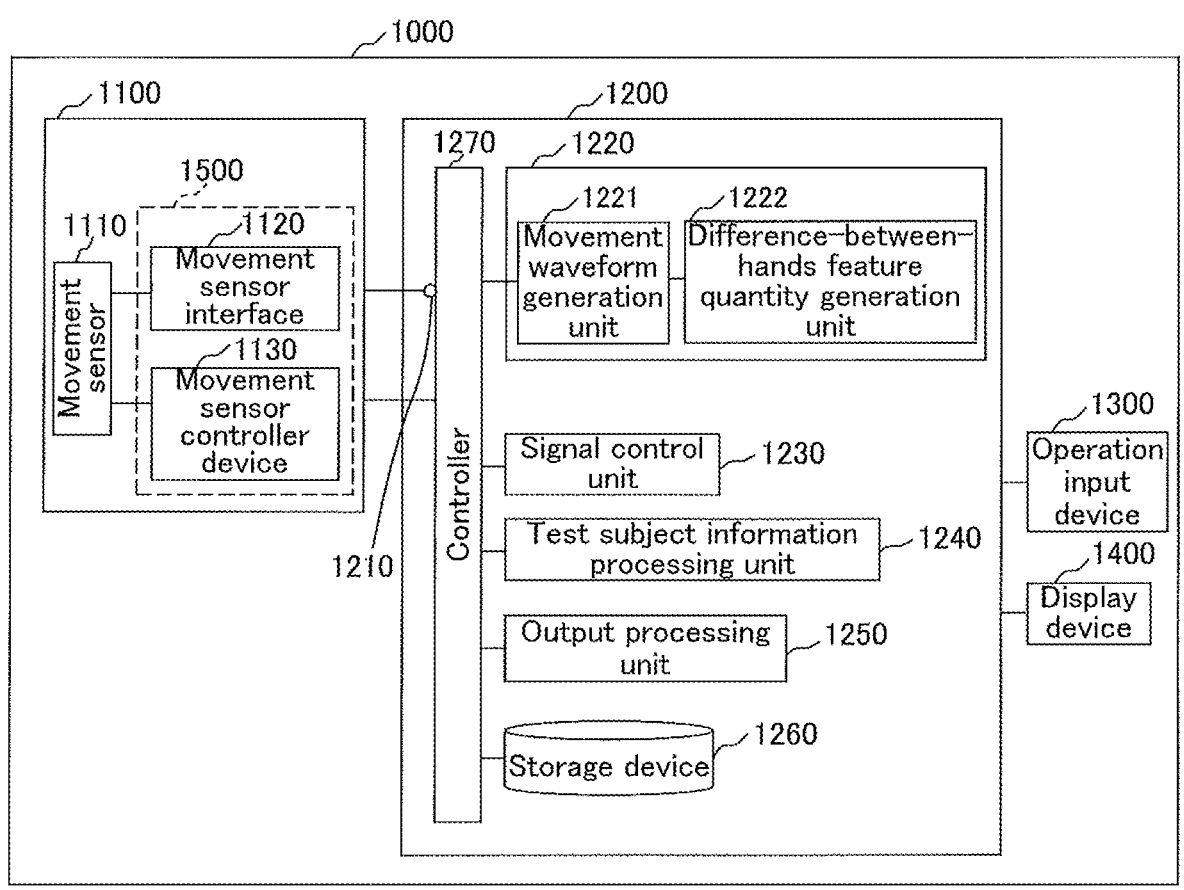
FIG. 1 is a block diagram illustrating an entire configuration of a brain dysfunction evaluation system according to an embodiment of the present invention.

As illustrated in FIG. 1, a brain dysfunction evaluation system 1000 according to this embodiment includes: a movement function measurement device 1100 configured to measure a hand finger movement task performed by a subject; a brain dysfunction evaluation apparatus 1200 configured to store and analyze data measured by the movement function measurement device 1100; an operation input device 1300 configured to receive an input of information on a test subject or the like; and a display device 1400 (which may also be referred to as a display unit) configured to output a result of the measurement or the analysis and display the outputted data.

The test subject herein is a subject who is subjected to a measurement by the movement function measurement device 1100. In this embodiment, the test subject is an individual who wants to take a test on whether or not he/she has developed dementia or how severe is his/her disease.

The movement function measurement device 1100 measures movements of hand fingers of the test subject, when the test subject carries out a finger movement task. The finger movement task used herein includes: finger-to-thumb tapping (in which the subject repeatedly opens and closes a thumb and an index finger of his/her hands as quickly and widely as possible) measured by a magnetic sensor; and a movement of touching or sliding a screen on a tablet terminal equipped with a touch panel sensor (a touch screen type sensor). The finger movement task used hereinafter means the finger-to-thumb tapping.

[Motor Function Measurement Device]

The movement function measurement device 1100 detects information on a finger movement task of a test subject (which may also be simply referred to as "movement information") in time series. The movement function measurement device 1100 acquires movement information on at least one of a distance, a velocity, an acceleration, a jerk (which is obtained by temporally differentiating the acceleration) of the test subject as time series data (waveform data).

The movement function measurement device 1100 includes a movement sensor 1110, a movement sensor interface 1120, and a movement sensor control device 1130.

The movement sensor interface 1120 and the movement sensor control device 1130 are accommodated in an accommodating device 1500, which is a single body, in this embodiment. Alternatively, the devices 1120, 1130 may not be accommodated in the single body.

<<Movement Sensor>>

Figure 2:
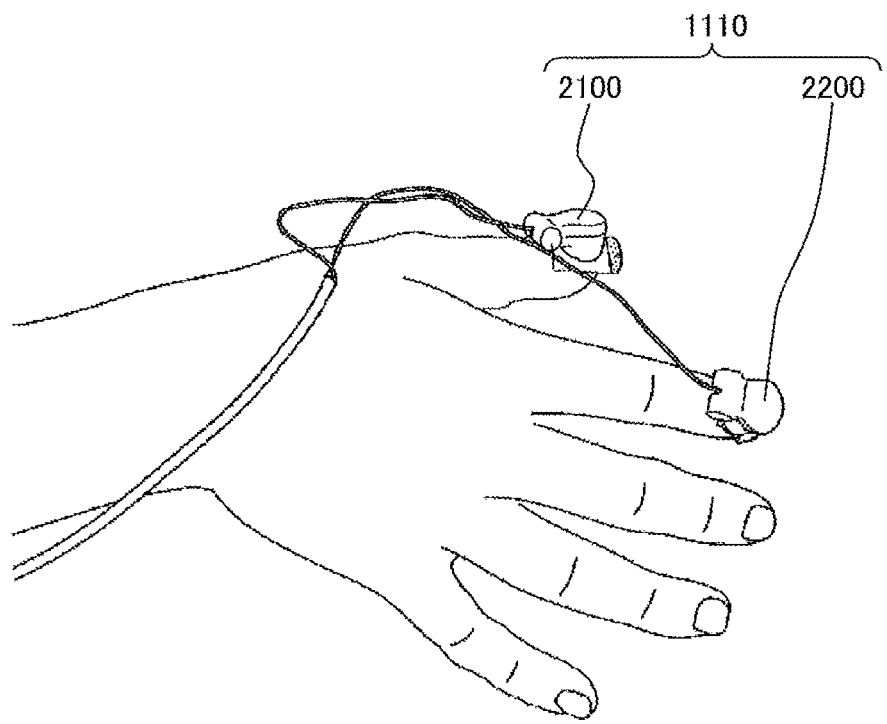
FIG. 2 is a diagram illustrating a diagram illustrating how a movement sensor is attached to a hand of a subject.

As illustrated in FIG. 2, the movement sensor 1110 includes: a transmitting coil 2100 which generates a magnetic field; and a receiver coil 2200 which receives (detects) the magnetic field.

The transmitting coil 2100 and the receiver coil 2200 are attached to a nail of a thumb and a nail of an index finger using, for example, a double faced adhesive tape, respectively. Alternatively, the transmitting coil 2100 and the receiver coil 2200 may be attached to the nail of the index finger and the nail of the thumb, respectively.

In this embodiment, the transmitting coil 2100 and the receiver coil 2200 are attached to the nails of the thumb and the index finger, respectively, or vice versa. The embodiment is not, however, limited to this. The coils 2100, 2200 may be attached to, for example, the fingers other than the nails.

The coils 2100, 2200 may be attached to, not limited to the thumb and the index finger, but to the thumb and a finger other than the index finger, for example, the thumb and a little finger. Parts to which the coils 2100, 2200 are attached are not limited to the nails or fingers of the test subject, but to, for example, parts neighboring the fingers such as a palm near the fingers. The transmitting coil 2100 and the receiver coil 2200 are thus attached to any of the nails, the fingers, and the parts neighboring the fingers of the test subject, as long as the finger movement task can be detected.

<<Movement Sensor Interface>>

The movement sensor interface 1120 (see FIG. 1): includes an analog to digital converter circuit; and is configured to convert waveform data of an analog signal detected by the movement sensor 1110, into waveform data of a digital signal with a predetermined sampling frequency, and introduces the converted digital signal into the movement sensor control device 1130 (see FIG. 1).

<<Movement Sensor Control Device>>

Figure 3:
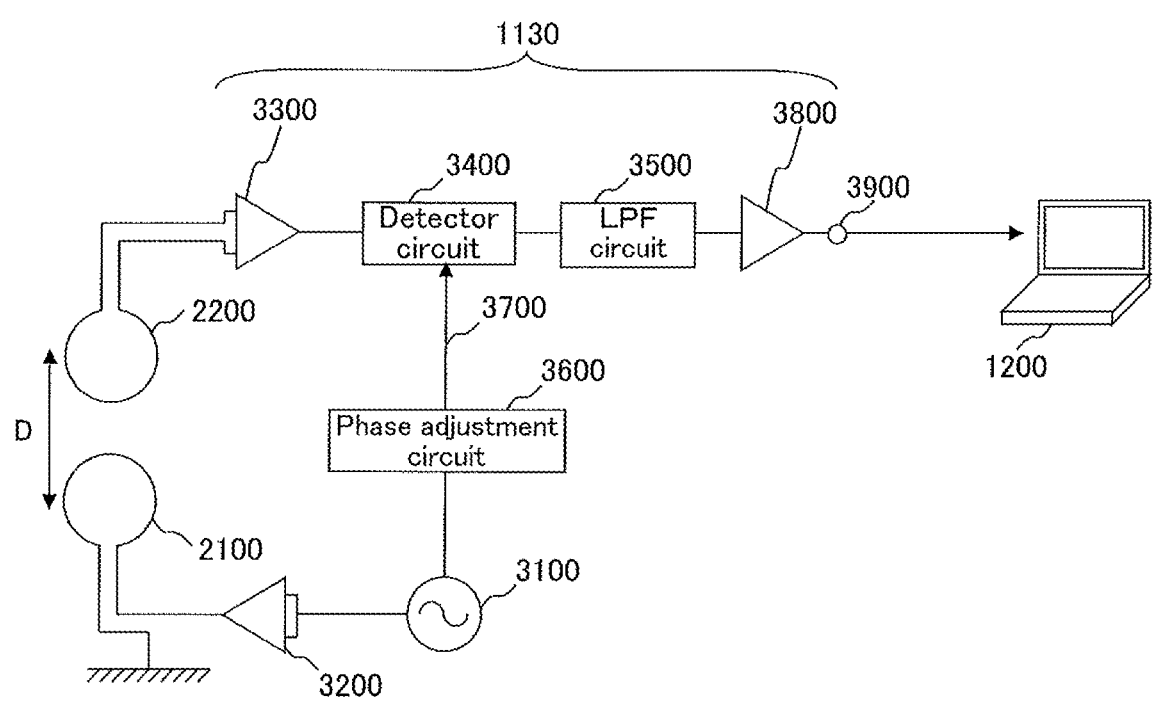
FIG. 3 is a diagram illustrating a configuration of a movement sensor controller.

FIG. 3 is a block diagram illustrating a configuration of the movement sensor control device 1130 (wherein the movement sensor interface 1120 is not shown). Next is described how the movement sensor control device 1130 acquires waveform data.

In FIG. 3, an alternative current (AC) generating circuit 3100 generates an AC voltage having a specific frequency (for example, 20 kHz). A current generating amplifier circuit 3200 converts the AC voltage having the specific frequency generated by the AC generating circuit 3100, into an alternating current having a specific frequency. The converted alternating current flows to the transmitting coil 2100. A magnetic field generated by the alternating current running in the transmitting coil 2100 makes the receiver coil 2200 generate an induced electromotive force.

The induced electromotive force generates another alternating current in the receiver cod 2200 (which has a frequency same as that of the AC voltage with the specific frequency generated by the AC generating circuit 3100). A pre-amplifier circuit 3300 amplifies the generated alternating current, of which signal after the amplification is inputted in a detector circuit 3400. The detector circuit 3400 detects the signal after the amplification, by the specific frequency generated by the AC generating circuit 3100 or a double frequency thereof. That is, a variation corresponding to fluctuations in voltage caused by a change in distance between the two fingers is extracted from a waveform containing a high frequency. For this purpose, a phase adjustment circuit 3600: adjusts a phase of the output of the AC generating circuit 3100; and introduces the adjusted output into a reference signal input terminal of the detector circuit 3400 as a reference signal 3700.

An output signal of the detector circuit 3400 passes through a LPF (Low-Pass Filter) circuit 3500 for removing a high frequency component; is amplified by the amplifier circuit 3800 so as to obtain a desired voltage; and is introduced in the brain dysfunction evaluation apparatus 1200. An output signal 3900 from the amplifier circuit 3800 indicates a voltage value corresponding to a relative distance D between the transmitting coil 2100 and the receiver coil 2200 attached to the thumb and the index finger, respectively (a conversion formula from the relative distance into the voltage value will be described hereinafter).

Description above has been made assuming a case where the movement sensor 1110 is a magnetic sensor. Alternatively, the movement sensor 1110 may be an acceleration sensor, a strain gauge, a high-speed camera, or the like. Or, a finger movement task may be measured by touching or sliding a screen on a tablet terminal, a smartphone, or the like, with one or more fingers.

[Brain Dysfunction Evaluation Apparatus]

The brain dysfunction evaluation apparatus 1200 (see FIG. 1) is configured to store and analyze data measured by the movement function measurement device 1100. The brain dysfunction evaluation apparatus 1200 used herein includes: a data input device 1210 configured to receive an output signal (time-series data) from the movement sensor control device 1130; a data processing device 1220 (which may also be referred to as an analysis unit) configured to analyze the output signal having been inputted; a signal control unit 1230 configured to transmit a signal for making the movement function measurement device 1100 start a measurement; a test subject information processing unit 1240; an output processing unit 1250 configured to process a result analyzed by the data processing device 1220, into a form such that the result can be outputted to the display device 1400; a storage device 1260 (which may also be referred to as a storage unit) configured to store therein data processed by the data processing device 1220 and the test subject information processing unit 1240; and a controller 1270 configured to control data transmission and reception, arithmetic processing, or the like.

<<Data Processing Device>>

The data processing device 1220 (see FIG. 1) calculates (generates) a movement waveform of a finger-to-thumb tapping performed by a test subject, based on the output signal transmitted from the data input device 1210 and received via the controller 1270; and thereby calculates an objective index representing how severe is a dementia of the test subject. The information obtained as described above is stored in the storage device 1260 where appropriate.

The data processing device 1220 includes: a movement waveform generation unit 1221; and a difference-between-hands feature quantity generation unit 1222.

<Movement Waveform Generation Unit>

The movement waveform generation unit 1221 (see FIG. 1) converts time-series data (waveform data) of the voltage output transmitted from the movement function measurement device 1100, into an appropriate movement waveform; temporally differentiates or integrates the converted movement waveform; and thereby complementarily generates a distance waveform, a velocity waveform, and an acceleration waveform (details of which will be described later).

The conversion formula for converting the voltage output (a voltage value) into the movement waveform (a relative distance waveform or the like) can be given as an approximate curve. The approximate curve is obtained as follows, for example. The test subject holds a calibration block with his/her two fingers. The calibration block is prepared by combining a plurality of blocks having different lengths (for example, blocks having 20, 30, and 60 mm in length) into one unit. Each time the test subject holds different parts having the different lengths (for example, 20, 30, and 60 mm) of the block, a voltage value and a distance value are measured. The approximate curve is calculated as a curve which minimizes a difference between a data set of the voltage value and the distance value, and an error thereof.

Figure 4:
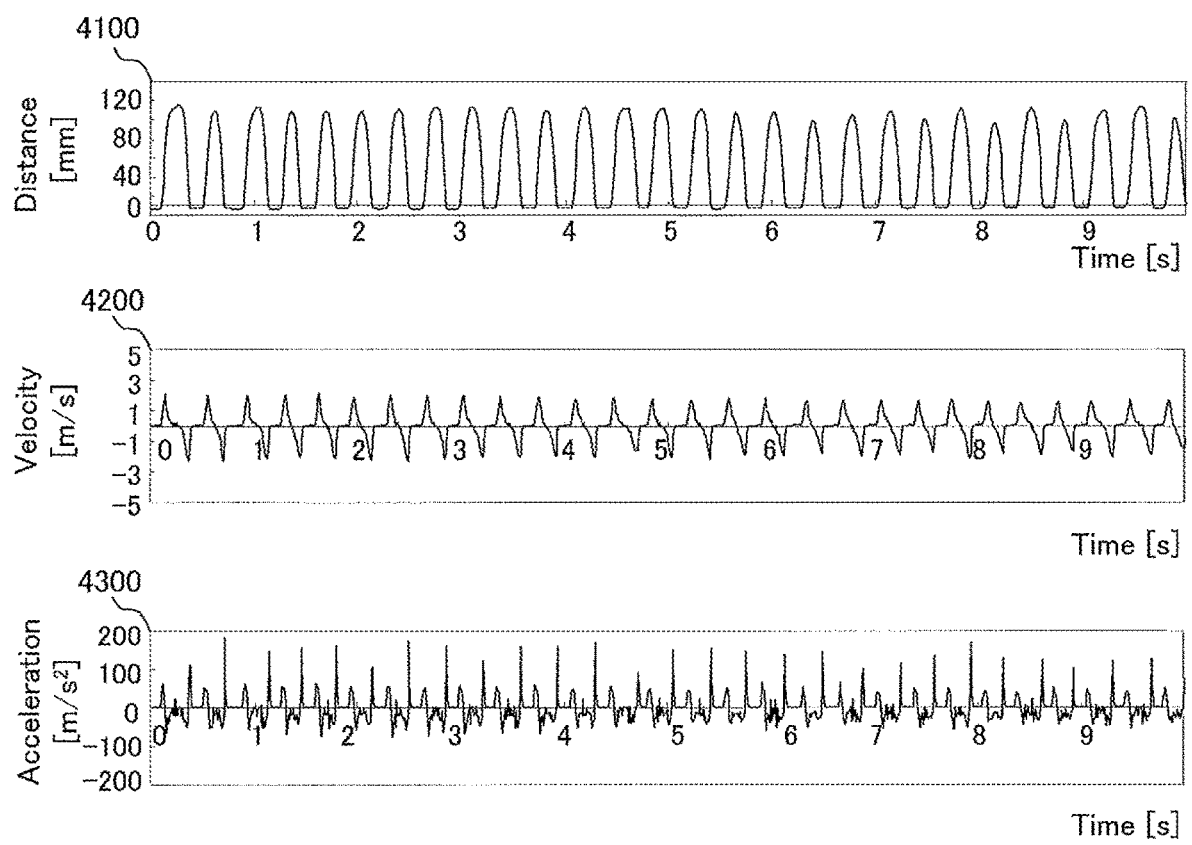
FIG. 4 is a diagram illustrating a movement waveform.

FIG. 4 is a diagram illustrating: a distance waveform 4100 which is obtained by converting the waveform data using the conversion formula; a velocity waveform 4200 which is obtained by temporally differentiating the distance waveform 4100; and an acceleration waveform 4300 which is obtained by temporally differentiating the velocity waveform 4200. The term "movement waveform" used herein includes, unless otherwise limited, at least one of a distance waveform, a velocity waveform, an acceleration waveform, and a jerk waveform. Note that even when a strain gauge, an acceleration meter, or the like is used as the movement function measurement device 1100, measurement of at least one of the movement waveforms (of distance, velocity, acceleration, and jerk) makes it possible to complementarily obtain the other movement waveforms by means of differentiation or integration.

<Difference-Between-Hands Feature Quantity Generation Unit>

The difference-between-hands feature quantity generation unit 222 (see FIG. 1) is configured to generate a difference-between-hands feature quantity which is a difference in respective finger movement tasks between the left and right hands, based on the movement waveform obtained from the movement waveform generation unit 1221. In this embodiment, the difference-between-hands feature quantity can be calculated in two different ways. One is that: respective feature quantities based on the movement waveforms of the left and right hands are separately calculated; and a difference between the two feature quantities are calculated (which may also be referred to as a first difference-between-hands feature quantity calculation method). The other is that: a time-series data which corresponds to a difference in the movement waveforms between the left and right hands; and calculates a feature quantity with respect to the difference waveform (which may also be referred to as a second difference-between-hands feature quantity calculation method). Next are described the two ways described above.

(First Difference-Between-Hands Feature Quantity Calculation Method)

[Feature Quantity Calculated Based on Movement Waveform of One Hand]

FIGS. 5A and 5B are a diagram illustrating names and definitions of feature quantities. Below are explained in detail some technical terms and feature quantities having feature quantities Nos. 5023 to 5029. Feature quantities having feature quantity Nos. 5001 to 5022 are as defined in FIGS. 5A and 5B, detailed description of which is thus omitted herefrom. Note that the terms "a feature quantity having a feature quantity No. 50XX" may also be simply referred to as "a feature quantity 50XX".

Figure 6:
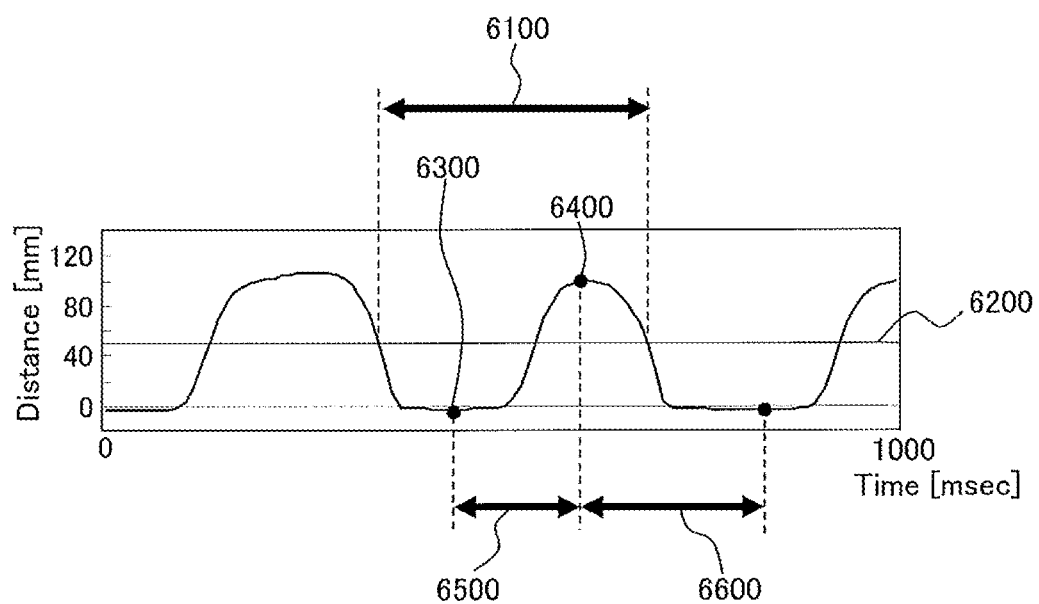
FIG. 6 is an explanatory diagram illustrating definition of terms of finger-to-thumb tapping.

As illustrated in FIG. 6, a period 6100 of finger-to-thumb tapping is defined as a time period from when a distance value crosses an average value 6200 of a distance waveform during a time period during which the distance waveform is measured, and at the same time, a velocity is smaller than 0, till when the same conditions are satisfied next time. A tap interval is defined as a length of the period. A point at which the distance value is the smallest in the period is referred to as a local minimum point 6300 of the distance waveform. The distance value at the point is referred to as a local minimal value. Similarly, a point at which the distance value is the largest in the period is referred to as a local maximum point 6400 of the distance waveform. The distance value at the point is referred to as a local maximal value. A movement starting from the local minimum point of a distance waveform until a next local maximal point thereof is defined as an opening movement 6500. A movement starting from the local maximal point of the distance waveform till a next local minimum point thereof is defined as a closing movement 6600.

A zero crossing count of a velocity waveform 5023 (or a feature quantity 5023; hereinafter the same, and names of the other feature quantities may also be represented similarly) (see FIG. 5B) is a value obtained by subtracting the tapping count 5019, from the number of times a velocity changes from a positive value to a negative value during a measurement time. Herein, the number of times the velocity changes from the positive value to the negative value may be substituted by the number of times the velocity changes from the negative value to the positive value.

The zero crossing count of the velocity waveform 5023 is a feature quantity for counting the number of times of up-and-down vibrations 7100 as illustrated in the distance waveform of FIG. 7A, other than large movements contained in the finger-to-thumb tapping. The count the velocity waveform crosses "0" corresponds to the number of times of the up-and-down vibrations of the distance waveform. A dementia patient has in general a larger number of times of such up-and-down vibrations in a distance waveform than that of a healthy subject.

Similarly, a zero crossing count of an acceleration waveform 5024 (see FIG. 5B) is a value obtained by subtracting the tapping count 5019, from the number of times an acceleration changes from a positive value to a negative value during a measurement time. Herein, the number of times the acceleration changes from the positive value to the negative value may be substituted by the number of times the acceleration changes from the negative value to the positive value.

As illustrated in FIG. 7B, the zero crossing count of the acceleration waveform 5024 is a feature quantity for counting not only the up-and-down vibrations but also a part 7200 at which strength of momentum un naturally fluctuates in a middle of the finger-to-thumb tapping. The count the acceleration waveform crosses "0" corresponds to the number of times of unnatural fluctuations in the momentum strength of the distance waveform. A dementia patient has in general a larger number of times of such unnatural fluctuations in the momentum strength than that of a healthy subject.

Figure 8:
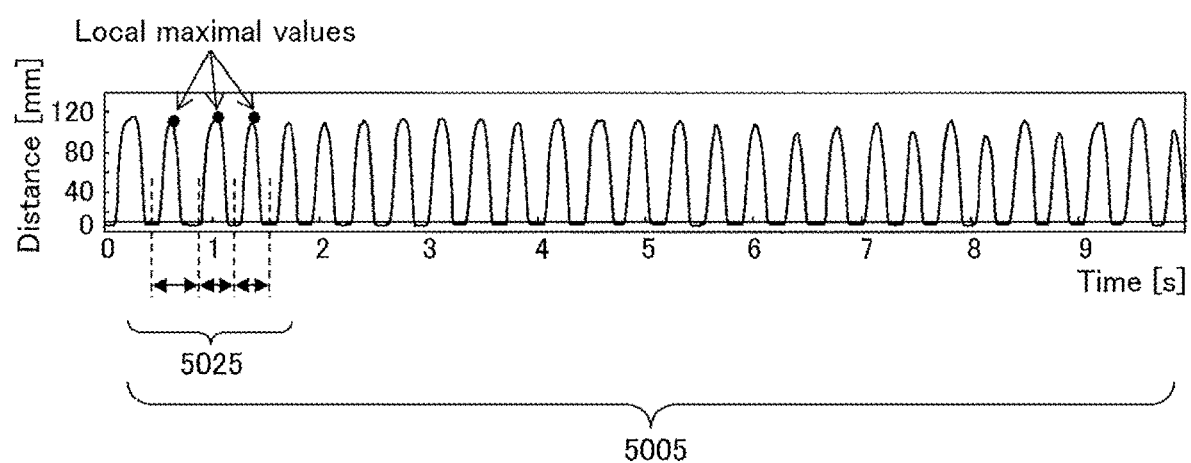
FIG. 8 is an explanatory diagram illustrating local standard deviation of amplitude of a distance waveform.

A local standard deviation of local maximal values of a distance waveform 5025 (see FIG. 5B) is, as illustrated in FIG. 8, an average value of standard deviations of local maximal values situated in "n" distances of the distance waveform (standard deviations of local maximal values of respective distances of distance waveforms for consecutive "n" periods), through the entire measurement time. Any number can be used as "n", as long as it is an integer of two or more and is smaller than the tapping count.

A local standard deviation of tap intervals 5026 (a feature quantity on dispersion of tapping time intervals) (see FIG. 5B) is an average value of standard deviations of neighboring "n" tap intervals through the entire measurement time. Any number can be used as "n", as long as it is an integer of two or more and is smaller than the tapping count.

It is contemplated that local vibrations in amplitude are large in dementia or similar diseases through the entire measurement time. Meanwhile, the local vibrations in amplitude of a healthy subject are not significant, though the amplitude gradually becomes smaller through the entire measurement time as the healthy subject becomes tired. A standard deviation of local maximal values of a distance waveform 5005 is obtained by calculating the standard deviations through the entire measurement time, which makes it difficult to show a difference between a dementia patient and a healthy individual. In contrast, the local standard deviation of local maximal values of a distance waveform 5025 can represent the difference therebetween, because local standard deviations continuously calculated through the entire measurement time show local variations in amplitude. Similarly, a local standard deviation of tap intervals 5026 can represent a difference therebetween.

Figure 9A:
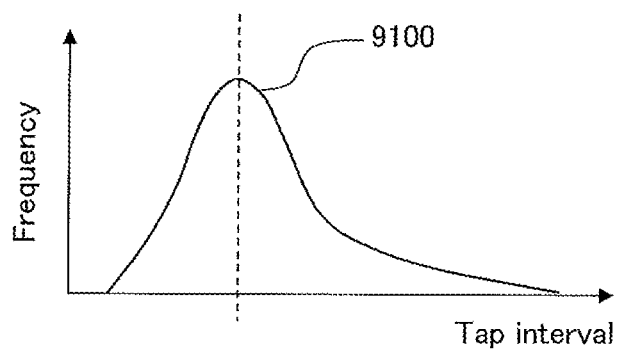
FIG. 9A is an explanatory diagram illustrating skewness of a frequency distribution of tap intervals.

Skewness of tap interval distribution 5027 (a feature quantity on dispersion of tapping time intervals) (see FIG. 5B) is skewness of a frequency distribution 9100 (a histogram) of tap intervals during the entire measurement time as illustrated in FIG. 9A. The skewness used herein is a statistical indicator representing asymmetry of a distribution, and can be obtained by, for example, dividing an average of a cube of a deviation (a difference from an average value) by a cube of a standard deviation.

A frequency distribution of tap intervals of a healthy individual is considered to take a shape close to a normal distribution. The frequency distribution of a dementia or similar disease patient may sometimes have a long tap interval. This makes the frequency distribution take a shape with a wider bottom toward a horizontal axis positive direction (on a right side of a horizontal axis in FIG. 9A). Distribution skewness of tap intervals 5027 can represent a property as described above. That is, it is contemplated that skewness of the frequency distribution of the healthy individual is close to "0", and that of the dementia patient takes a relatively large value.

Figure 9B:
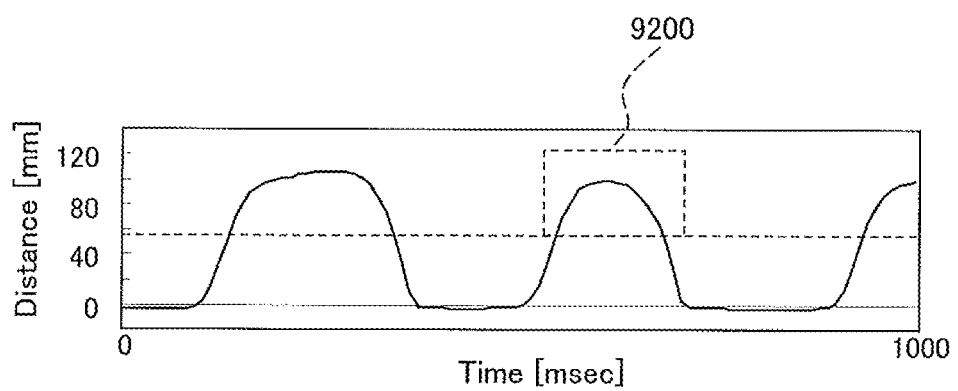
FIG. 9B is an explanatory diagram illustrating a near-local-maximal-point peakedness of a distance waveform.

A near-local-maximal-point peakedness 5028 (see FIG. 5B) is an average value of peakednesses of local maximal points of the distance waveform through the entire measurement time. The peakedness used herein is a statistical indicator representing a degree of how sharp a distribution curve is. The peakedness can be obtained by, for example, dividing an average of the fourth power of deviations (differences from respective average values) by the fourth power of standard deviations. As illustrated in FIG. 9B, the peakedness is herein calculated assuming that a distance waveform having a certain value (for example, 55 mm) or more is taken as a near-local-maximal-point distance waveform 9200.

The near-local-maximal-point peakedness 5028 is considered to represent muscle stiffness (muscle rigidity). Stiff muscle may cause not a smooth but an abrupt switching between an opening movement and a closing movement, making a distance waveform near a local maximal point sharp.

[Trajectory of Chaotic Time Series]

Figure 10A:
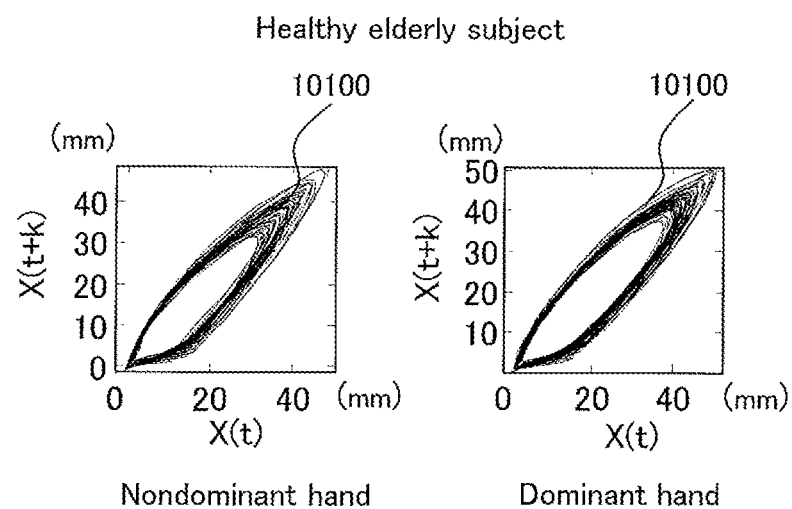
FIGS. 10A and 10B are explanatory diagrams illustrating trajectories in chaotic time series analyses.
Figure 10B:
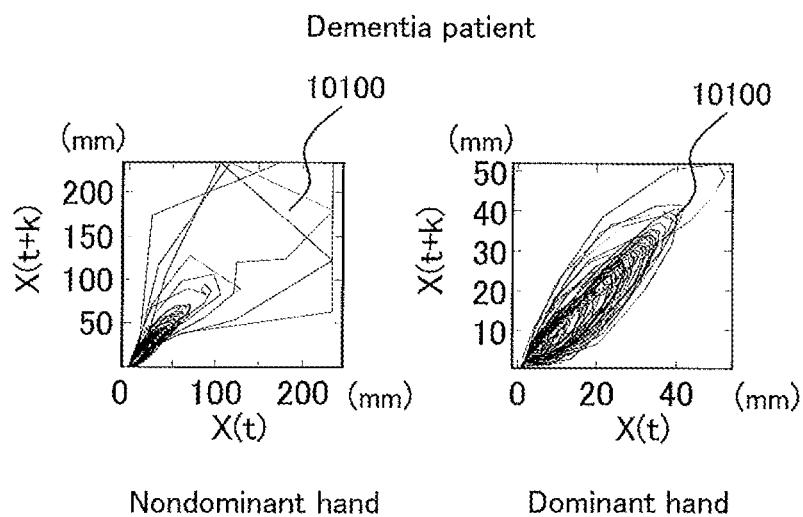

Stability of time delay trajectory 5029 (see FIG. 5B) used herein is, as illustrated in FIGS. 10A and 10B, a value (a feature quantity) representing stability of a trajectory 10100 of Movement waveform X(t) at Time t and Movement waveform X(t+k) at Time t+k. The trajectory is generated by plotting a finger-to-thumb tapping with X(t) and X(t+k) on horizontal and vertical axes, respectively (time delay k is a predetermined constant value, for example, 20 msec or the like). The trajectory plotting described above is used in a field of chaotic time series analysis for evaluating periodicity or stability of time-series data. Stability of finger-to-thumb tapping can be evaluated based on a form of the trajectory. The trajectory of X(t) and X(t+k) 10100 of a healthy elderly subject draws ellipses inclined upward right with respect to both a dominant hand and a nondominant hand, and demonstrates stability in any period (see FIG. 10A). The trajectory of a dementia patient with respect to a dominant hand also draws ellipses, indicating stability. The trajectory of the dementia patient with respect to a nondominant hand is, however, indicative of instability (see FIG. 10B).

The stability of time delay trajectory 5029 (a feature quantity) for evaluating stability is obtained by calculating an area of a difference between a trajectory for each period and an innermost trajectory and calculating an average value thereof. The larger the stability of time delay trajectory 5029, the less stable the periods of finger-to-thumb tapping during the measurement time. Note that the trajectory as an attractor is herein drawn with the two axes, X(t) and X(t+k). The trajectory may be drawn with three or more axes, such as X(t), X(t+k), and X(t+2k).

In the feature quantities having the feature quantity Nos. 5001 to 5029 illustrated in FIGS. 5A and 5B, instead of the standard deviation, another statistical indicator showing data variability such as dispersion may be used. In order to equalize data on subjects' hands different in size, the data may be standardized using a distance value when the two fingers of interest are extended as wide as possible.

[Difference-Between-Hands Feature Quantity]

The feature quantities 5001 to 5029 of the finger-to-thumb tapping for each of the dominant hand and the nondominant hand are calculated. A feature quantity of the dominant hand is then subtracted from a feature quantity of the nondominant hand, which is referred to as a difference-between-hands feature quantity. As a decline in cognitive function progresses, a difference in movement functions between the dominant hand and the nondominant hand is considered to become larger. On the other hand, the dominant hand and the nondominant hand are considered to reflect inherent physical capability of a test subject. The difference-between-hands feature quantity can thus indicate how severe a decline in cognitive function is, after the inherent physical capability of the test subject is offset.

Figure 11A:
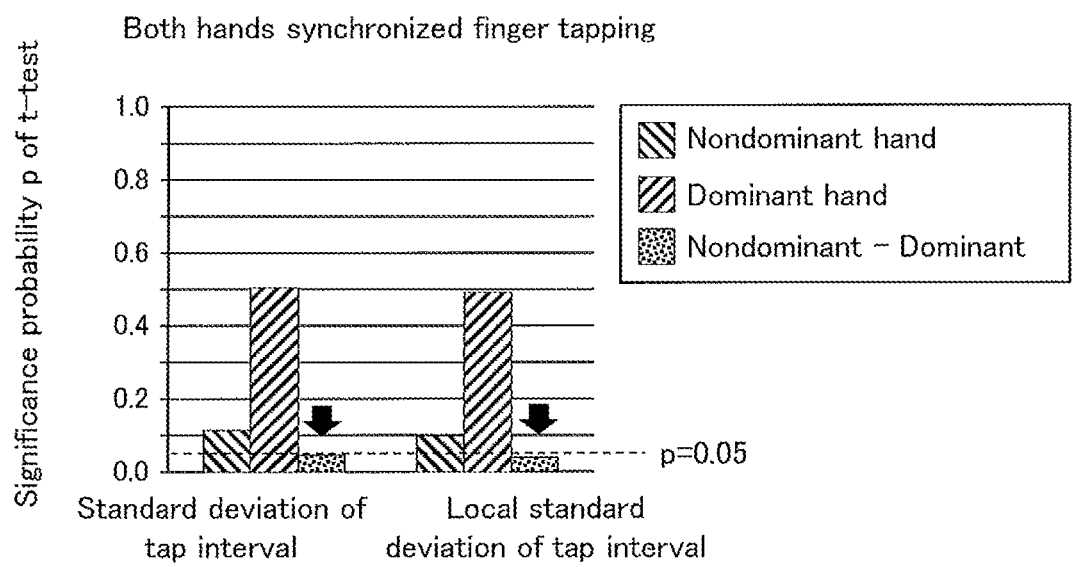
FIGS. 11A and 11B are diagrams illustrating significance probabilities when t-test is applied to difference-between-hands feature quantities of a healthy elderly subject group and a dementia patient group.
Figure 11B:
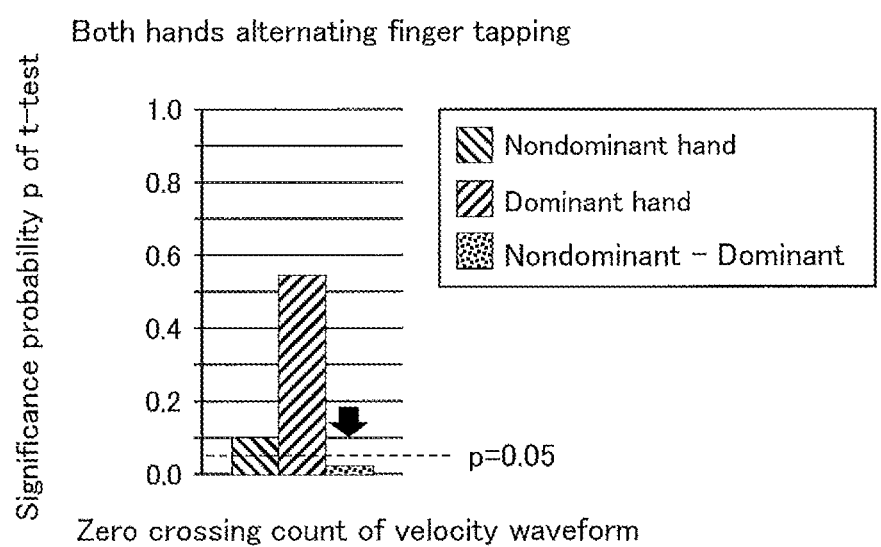

FIGS. 11A and 11B illustrate significance probabilities which indicate whether or not there is a significant difference in difference-between-hands feature quantities between a healthy elderly subject and a dementia patient. As illustrated in FIG. 11A, in both hands synchronized finger tapping (finger tapping in which the fingers of both hands are opened and closed simultaneously) with respect to the standard deviation of tap intervals (the feature quantity 5022) (which is a feature quantity on variations of tapping time intervals) and a local standard deviation of tap intervals (the feature quantity 5026), a difference-between-hands feature quantity has a smaller significance probability than a feature quantity of each of the nondominant hand and the dominant hand, meaning that there is a significant difference (the significance probability $p<0.05$). As illustrated in FIG. 11B, in both hands alternating finger tapping (finger tapping in which the fingers of both hands are opened and closed), with respect to the zero crossing count of a velocity waveform (the feature quantity 5023), a difference-between-hands feature quantity has a smaller significance probability than a feature quantity of the nondominant hand and the dominant hand, meaning that there is a significant difference (significance probability $p<0.05$).

When the difference-between-hands feature quantity of the feature quantities 5001 to 5029 are calculated, instead of subtracting the feature quantity of the dominant hand from the feature quantity of the nondominant hand, the feature quantity of the nondominant hand may be subtracted from the feature quantity of the dominant hand. Or, the feature quantity of the nondominant hand may be divided by the feature quantity of the dominant hand, and vice versa. That is, respective feature quantities of both hands are used for obtaining a difference (a subtraction value in which one value is subtracted from another) or a quotient value obtained by dividing one value by another, which allows difference-between-hands feature quantity to be calculated.
(Second Difference-Between-Hands Feature Quantity Calculation Method)

Next is described an example of how to calculate a feature quantity after a difference in movement waveforms between both hands is calculated, as a second difference-between-hands feature quantity calculation method.
[Variation Cycles of Nondominant Hand and Dominant Hand]

An ideal finger-to-thumb tapping task with both hands opening and closing simultaneously (both hands synchronized finger tapping) has no displacement in respective waveforms of both hands. It is easy for a healthy subject to simultaneously move his/her both hands without displacement. Even if any displacement is generated, the subject can promptly adjust his/her movement so as to eliminate the displacement. It is difficult, however, for a dementia patient presenting with a progressive decline in cognitive function to move both hands in synchronization. It is also difficult to recognize and eliminate displacement, if any.

Figure 12A:
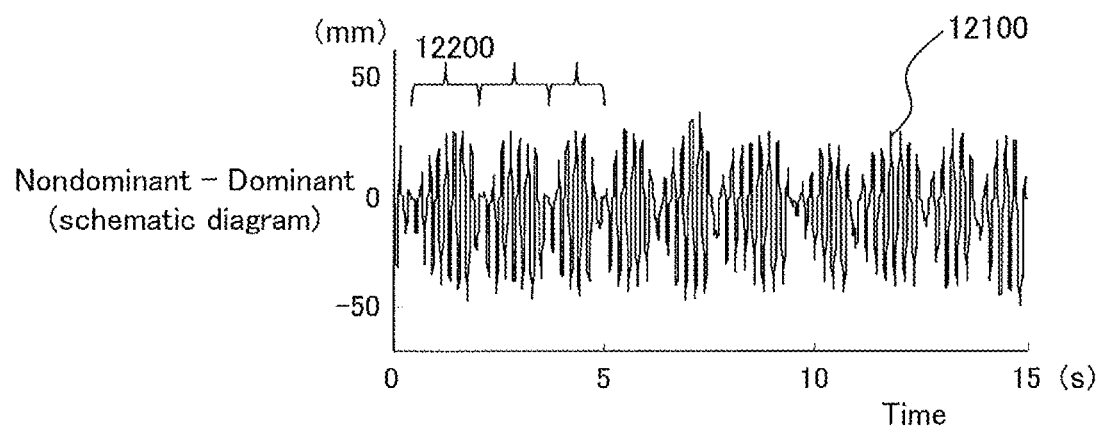
FIG. 12A is an explanatory diagram illustrating a variation cycle of a difference-in-both-hands waveform.

FIG. 12A illustrates a difference-in-both-hands waveform 12100 which is obtained by calculating a difference in respective movement waveforms (time-series data) between both hands. The difference-in-both-hands waveform 12100 always takes a value "0", if there is no displacement between the waveforms of both hands. Meanwhile, the difference-in-both-hands waveform 12100 takes a large value, if there is large displacement. The difference-in-both-hands waveform 12100 contains two types of frequencies: a first frequency which is same as that of finger-to-thumb tapping (about 2 to about 5 Hz for a healthy individual); and a second frequency as a variation cycle 12200 for eliminating displacement between both hands.

Figure 12B:
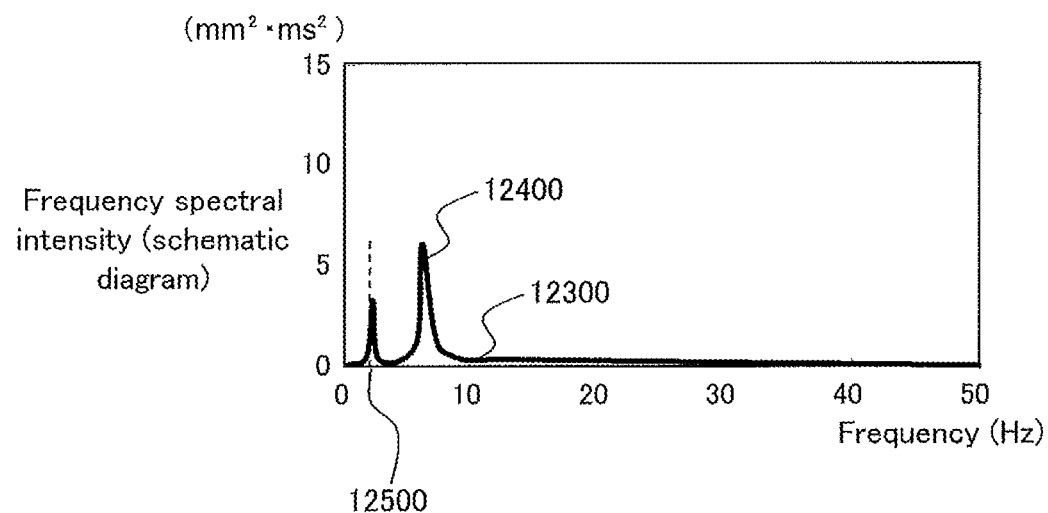
FIG. 12B is an explanatory diagram illustrating a frequency peak of the difference-in-both-hands waveform.

FIG. 12B illustrates a frequency spectrum (frequency component) 12300 which is calculated by applying Fourier transform to the difference-in-both-hands waveform. Respective frequencies corresponding to the two strongest peak values of the frequency spectrum 12300 are extracted and taken as a first frequency 12400 and a second frequency 12500 (a difference-between-hands feature quantity) which is smaller than the first frequency 12400. The larger the second frequency 12500, the more quickly the displacement is eliminated and the smaller a decline in cognitive function. In other words, it can be determined that the decline in cognitive function is large, if, for example, the second frequency 12500 is not more than a prescribed threshold (for example, about 1 Hz).

<<Signal Control Unit>>

The signal control unit 1230 (see FIG. 1) transmits a signal for starting a measurement to the movement function measurement device 1100 in response to an operation signal transmitted from the operation input device 1300. The movement function measurement device 1100 is in standby state when no measurement is performed, and enters a state ready for measurement on receipt for the signal from the signal control unit 1230.

<<Test Subject Information Processing Unit>>

The test subject information processing unit 1240 (see FIG. 1) manages information, using a test subject DB (Data Base) of the storage device 1260 which stores therein test subject information or information on analysis results.

More specifically, the test subject information processing unit 1240 performs four major processings as follows, making use of the test subject DB: 1) register, modify, delete, search, and sort the test subject information; 2) associate the test subject information with measurement data; 3) register, modify, and delete a result of analysis of the measurement data (add, modify, and delete an appropriate item); and 4) if statistical processing is performed, register, modify, and delete a result of the statistical processing.

The test subject information registered in the test subject DB includes: a test subject ID (Identifier), a name, a birth date, an age, a body height, a body weight, a disease name, and comments on the test subject. Note that information management performed by the test subject information processing unit 1240 can be easily realized using known program and data configuration.

<<Output Processing Unit>>

The output processing unit 1250 (see FIG. 1) makes the display device 1400 display the test subject information registered in the test subject DB or information on the analysis result or the like in a display style easy to visually understand, using an appropriate graph or table format. The output processing unit 1250 may or may not simultaneously display all of the analysis result described above, and may display only an item selected by an operator via the operation input device 1300.

<<Controller>>

The controller 1270 (see FIG. 1) includes a CPU (Central Processing Unit), a ROM (Read Only Memory), a RAM (Random Access Memory), or the like.

Respective functions of the units in the data processing device 1220, the signal control unit 1230, the test subject information processing unit 1240, and the output processing unit 1250 are realized by loading appropriate programs or data stored in the storage device 1260, into the controller 1270, and by executing an arithmetic processing.

[Operation Input Device]

The operation input device 1300 (see FIG. 1) is configured to receive an entry of the test subject information by an operator of the brain dysfunction evaluation system 1000; and can be realized by means of a keyboard, a mouse, or the like. An entry screen may be displayed in a display as a user interface for assisting the operator in entering the test subject information.

[Display Device]

The display device 1400 (see FIG. 1) is configured to output the test subject information or movement information processed by the data processing device 1220, and can be realized by, for example, a LCD (Liquid Crystal Display), a CRT (Cathode Ray Tube) display, a printer, or the like.

(Example of Screen)

Figure 14:
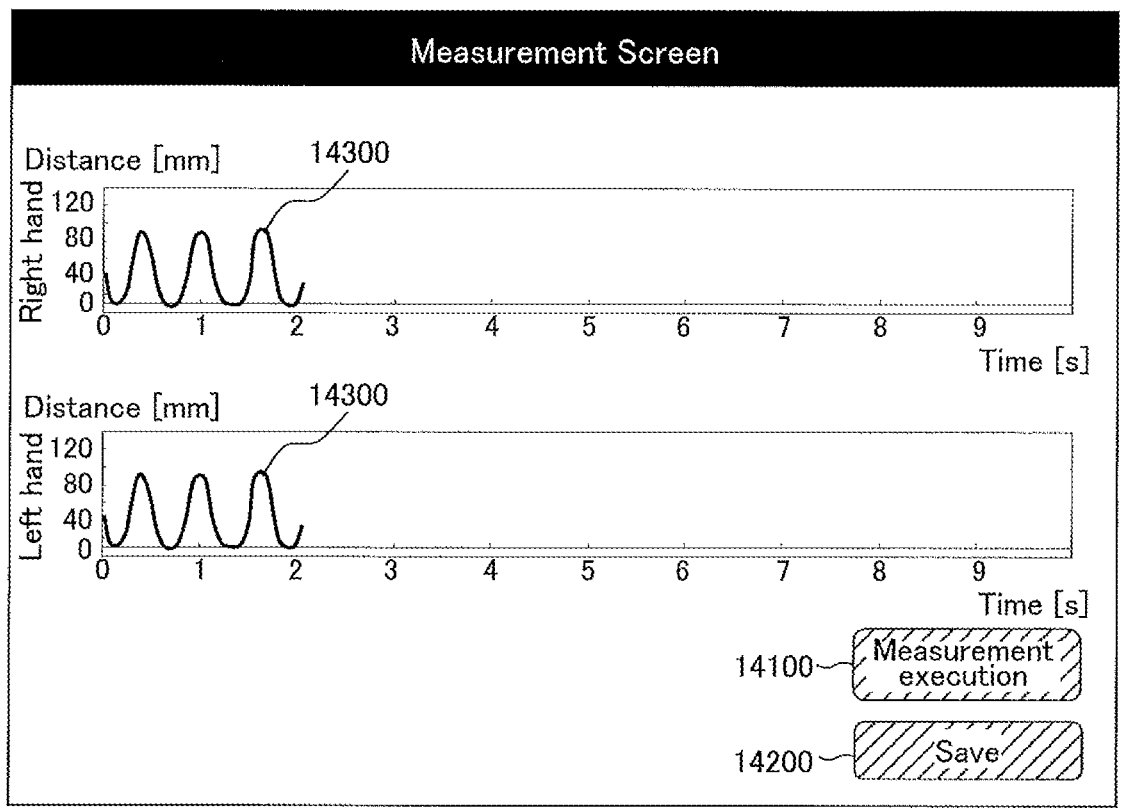
FIG. 14 is a diagram illustrating a measurement screen.

Next is described an example of a screen displayed in the display device 1400 with reference to FIG. 13 and FIG. 14.

As illustrated in FIG. 13, an entry screen of the test subject information includes a test subject ID entry field 13100, a name entry field 13200, a birth date entry field 13300, a handedness entry field 13400, and a remarks entry field 13500. A measurer (for example, a medical doctor) enters appropriate information in those entry fields and clicks a save button 13600 with a mouse, in response to which the test subject information processing unit 1240 stores the entered test subject information in the storage device 1260. Information on handedness is used for calculation performed by the difference-between-hands feature quantity generation unit 1222.

When a measurer (for example, a medical doctor) clicks a measurement execution button 14100 on the measurement screen for displaying a movement waveform under measurement, as illustrated in FIG. 14, the measurement is started and a movement waveform 14300 under measurement is drawn. When the measurer clicks a save button 14200 after completion of the measurement, the movement waveform and a result of analysis obtained by the respective units of the data processing device 1220 are saved.

[Advantageous Effects]

The brain dysfunction evaluation system 1000 according to this embodiment can evaluate a degree of severity of dementia using a difference-between-hands feature quantity calculated by the difference-between-hands feature quantity generation unit 1222.

In this embodiment, a program to be executed by a computer constituting the brain dysfunction evaluation system 1000 can be created and installed in the computer. This allows the computer to realize various functions based on the program.

(Variation)

Next is, described a variation of the brain dysfunction evaluation system 1000.

[Variation of Configuration of Brain Dysfunction Evaluation System]

Figure 15:
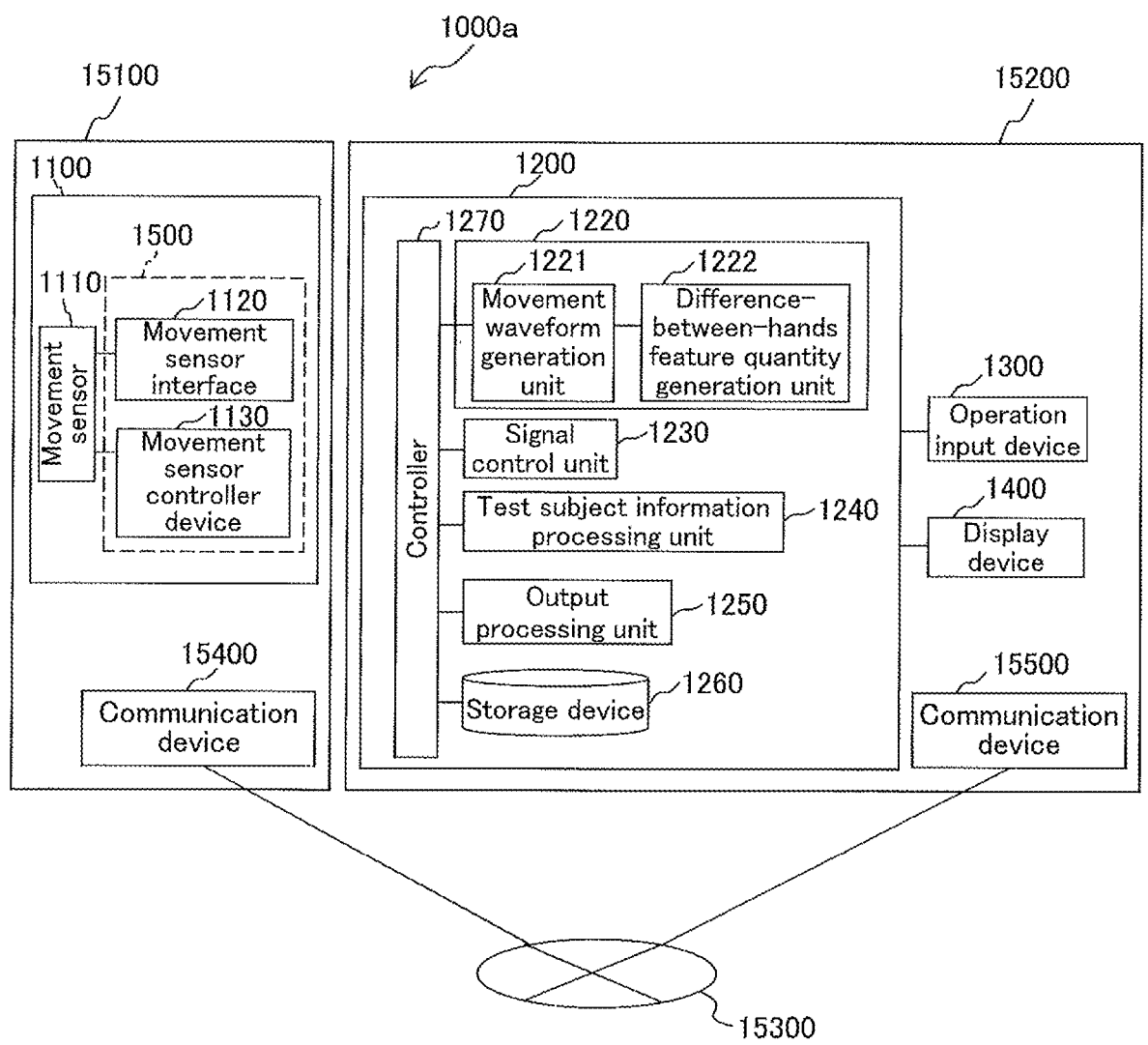
FIG. 15 is a block diagram illustrating another configuration of a brain dysfunction evaluation system including a terminal device and a server according to a variation of the present invention.

FIG. 15 is a diagram illustrating an example of an entire configuration of a brain dysfunction evaluation system 1000a according to a variation of the present invention. The brain dysfunction evaluation system 1000a illustrated in FIG. 15 realizes functions substantially same as those of the brain dysfunction evaluation system 1000 illustrated in FIG. 1, but performs the functions separately with a terminal device 15100 and a server 15200 which are connected each other via a communication network 15300.

In the brain dysfunction evaluation system 1000a, the terminal device 15100: presents a movement task to a test subject; and acquires data on the movement task of the test subject. The server 15200: receives the data on the movement task of the test subject acquired by the terminal device 15100, via the communication network 15300; and evaluates how severe a decline in cognitive function of the test subject is, based on the data on the movement task of the test subject. Except the described above, the configuration and the functions of the brain dysfunction evaluation system 1000a are same as those of the brain dysfunction evaluation system 1000 illustrated in FIG. 1, description of which is thus focused on only those different from each other.

The terminal device 15100 includes a communication device 15400 (which may also be referred to as a first communication device) connected to the communication network 15300, in addition to the movement function measurement device 1100 of the brain dysfunction evaluation system 1000 illustrated in FIG. 1. The server 15200 includes a communication device 15500 (which may also be referred to as a second communication device) connected to the communication network 15300, in addition to the brain dysfunction evaluation system 1000 illustrated in FIG. 1, the brain dysfunction evaluation apparatus 1200, the operation input device 1300, and the display device 1400. Information transmitted from the communication device 15400 to the communication device 15500 via the communication network 15300 is time-series data of a movement waveform or the like.

The terminal device 15100 having the configuration as described above can be realized by a personal computer, a tablet terminal, a smartphone, or the like of a medical doctor, a test subject, a caregiver thereof, or the like. The server 15200 can be realized by a high-performance personal computer, a work station, a general-purpose computer, or the like. Note that one unit of the server 15200 may be connected to a plurality of the terminal devices 15100 via the communication network 15300.

In the brain dysfunction evaluation system 1000a, the terminal device 15100 simply acquires data on a movement task of a test subject. This means that if by any chance, the terminal device 15100 is lost, data on a degree of cognitive impairment of a test subject is prevented from leaking. Further, a result of evaluating the cognitive impairment or the like of the test subject can be stored in the storage device 1260 of the server 15200. This means that a medical doctor, a nurse, a caregiver, and the others concerned can have an easy access to the result. The server 15200 in the brain dysfunction evaluation system 1000a allows an easy connection to a system which manages another medical and health information, such as an electronic health record system, a medication record system, and a healthcare system.

The present embodiments have been explained as above. The present invention is not, however, limited to the above-described embodiments but includes different kinds of variations. For example, the above-described embodiments are intended to be illustrative of the present invention in an easily understandable manner and the present invention is not limited to the one that includes all of the components explained in the embodiments. Part of a configuration of an embodiment of the present invention can be substituted by that of another embodiment. Part or all of a configuration of an embodiment of the present invention can be added to that of another embodiment. Further, various changes in specific configurations and processings are possible within a scope not departing from the gist of the present invention.

符号の説明＜削除＞

The invention claimed is:

1. A sensor system for evaluating brain dysfunction comprising:
   one or more movement sensors configured to detect a finger movement task of a test subject;
   a memory configured to store therein time-series data on the finger movement task of each of both hands of the test subject;
   a processor configured to analyze the time-series data stored in the memory; and
   a display configured to display an analysis result analyzed by the processor,
   wherein the processor is communicatively coupled with the memory, the one or more movement sensors and the display, and the processor is configured to:

generate a movement waveform for each of the both hands corresponding to the time-series data stored in the memory, generate a feature quantity representing stability of a trajectory of the movement waveform of each of the both hands, by plotting Movement waveform X(t) at Time t on a horizontal axis and Movement waveform X(t+k) at Time t+k on a vertical axis, wherein k is a predetermined constant representing a time delay, calculate either a difference in the generated feature quantities of the both hands or a quotient of the generated feature quantities of the both hands, as a difference-between-hands feature quantity which represents a difference in respective finger movement tasks between the both hands for evaluating a degree of severity of brain dysfunction.

2. A brain dysfunction evaluation method using a sensor system, comprising:

one or more sensors configured to detect a finger movement task of a test subject;

a memory configured to store therein time-series data on the finger movement task of each of both hands;

a processor configured to analyze the time-series data stored in the memory; and a display configured to display an analysis result analyzed by the processor, the brain dysfunction evaluation method comprising the steps of:

generating a movement waveform for each of the both hands corresponding to the time-series data stored in the memory;

generating a feature quantity representing stability of a trajectory of the movement waveform of each of the both hands by plotting Movement waveform X(t) at Time t on a horizontal axis and Movement waveform X(t+k) at Time t+k on a vertical axis, wherein k is a predetermined constant representing a time delay; and calculating either a difference in the generated feature quantities of the both hands or a quotient of the generated feature quantities of the both hands, as a difference-between-hands feature quantity which represents a difference in respective finger movement tasks between the both hands for evaluating a degree of severity of brain dysfunction.

* * * * *